United States Patent
Saffell et al.

(10) Patent No.: US 6,746,587 B2
(45) Date of Patent: Jun. 8, 2004

(54) ELECTROCHEMICAL GAS SENSOR

(75) Inventors: John R. Saffell, Stoke Charity (GB); Darryl H. Dawson, Chelmsford (GB)

(73) Assignee: Alphasense Limited, Essex (GB)

(*) Notice: Subject to any disclaimer, the term of this patent is extended or adjusted under 35 U.S.C. 154(b) by 52 days.

(21) Appl. No.: 10/001,924

(22) Filed: Nov. 15, 2001

(65) Prior Publication Data

US 2002/0121438 A1 Sep. 5, 2002

(30) Foreign Application Priority Data

Nov. 15, 2000 (GB) .............................................. 0027877

(51) Int. Cl.[7] ................................................ G01N 27/31
(52) U.S. Cl. ...................................... 204/432; 204/41.5
(58) Field of Search ................................ 204/431, 432, 204/412, 415; 205/782, 782.5, 783

(56) References Cited

U.S. PATENT DOCUMENTS

| 4,525,704 A | * | 6/1985 | Campbell et al. | |
| 5,284,566 A | | 2/1994 | Cuomo et al. | 204/412 |
| 5,395,507 A | * | 3/1995 | Aston et al. | |
| 5,632,875 A | * | 5/1997 | Chapples et al. | |
| 5,635,627 A | * | 6/1997 | Bytyn | |

FOREIGN PATENT DOCUMENTS

| EP | 0298570 | 7/1988 | .......... G01N/27/46 |
| GB | 2270982 A | 3/1994 | .......... G01N/27/404 |

* cited by examiner

*Primary Examiner*—Alex Noguerola
(74) *Attorney, Agent, or Firm*—Mayer Fortkort & Williams, PC; Michael P. Fortkort, Esq.

(57) ABSTRACT

An electrochemical gas sensor comprises: a working electrode for exposure to a gas to be sensed; a counter electrode having an outer periphery; a reservoir for electrolyte; wick means providing a path for electrolyte to pass from the reservoir, around a first part or parts of the outer periphery of the counter electrode to provide electrolytic continuity between the counter electrode and the working electrode; and a gas diffusion means providing a path for gas to diffuse to or from a second part or parts of the outer periphery of the counter electrode.

13 Claims, 4 Drawing Sheets

ELECTROCHEMICAL GAS SENSOR

FIELD OF THE INVENTION

The present invention concerns an electrochemical gas sensor for sensing a target gas, the sensor comprising a working electrode and a counter electrode, and particularly relates to a sensor in which a reagent gas needs to be supplied to or removed from the counter electrode. Applications of the sensor include the detection of toxic or other gases in an atmosphere, particularly the detection of carbon monoxide in air, where it is important that oxygen is supplied to the counter electrode.

BACKGROUND OF THE INVENTION

In recent years the need for detection and measurement of toxic, noxious and irritating gases in the environment has increased as public awareness of the potential dangers and corporate awareness of potential accidents and death by gas poisoning has increased.

Numerous sensing systems have been developed to measure such gaseous components. Although direct chemical methods exist, other analytical techniques such as gas chromatography, infrared absorption and molecular fluorescence have all been used to quantify toxic or noxious gas concentrations in the atmosphere.

However, chemical methods of gas detection continue to dominate. These chemical methods depend on measuring a change in a property of a sensing material. Conductivity, dielectric constant, mass change or semiconductor behaviour have all been used to monitor toxic gas concentration, either qualitatively or quantitatively. Colourimetric detection tubes (see K Grosskop "Angew.Chemie", vol 63, pages 306–308, 1962) have been used for several decades. However, the above techniques suffer from either a lack of discrimination of the gas species or from excessive power demands in the case of solid state semiconductor devices which must operate at typically 500° C.

The most popular gas detection method is wet electrochemistry using an electrochemical gas sensor in the form of an electrochemical cell comprising a working electrode and a counter electrode. A target gas or vapour reacts electrochemically with the working electrode of an electrochemical gas sensor. The result of the reaction at this working electrode can be determined by measuring either a voltage change (potentiometry) or a current generated by the reaction (amperometry).

In electrochemical gas sensors, the target gas or vapour reacts at the working electrode of the electrochemical cell and the current generated by this electrochemical reaction is balanced by a reaction at the counter electrode, with an intervening body of electrolyte between the electrodes providing electrolytic continuity. The electrochemical cell must be part of a complete electrical circuit, so that the current generated at the working electrode must be conducted away from the cell to a circuit to measure this current. In addition, the electrochemical cell will usually include a third electrode (constituting a reference electrode) which sets a characteristic potential of the electrochemical cell, to assist in regulating the electrochemical reaction at the working electrode. In amperometry an external potentiostat circuit measures the reference electrode potential relative to the working electrode and supplies adequate current into the counter electrode, forcing a reaction at the counter electrode to balance the working electrode reaction. The potentiostat circuit not only provides the current required for the counter electrode but also ensures that the working electrode is operating at the same potential as the reference electrode, or if a bias voltage is inserted, then at a controlled bias potential relative to the reference electrode.

Like the working electrode, the counter and reference electrodes also require conductors either to allow electrical monitoring of the reference electrode potential or to complete the electric circuit to the counter electrode. As noted above, at the counter electrode a reaction occurs that is opposite to the reaction at the working electrode, i.e. if the working electrode is oxidising a gas then the counter electrode will be reducing another species. This reaction at the counter electrode will generate a by-product which may be a gas, a solution species or precipitate an ion. The creation or consumption of chemical components at both the working and counter electrodes requires that these required or resultant components are transported either to or away from the electrochemically surface active.

One major concern with electrochemical amperometric gas sensors is ensuring that the electrolyte maintains continuous contact with the electrodes and between the electrodes. This has been done by changing the state of the electrolyte; alternative forms include electrolyte gels and solid state ion conductive membranes. However, the most popular method for transporting electrolyte within electrochemical cells, including fuel cells, batteries and gas sensors, is the use of a wicking or wetting material which immobilises the electrolyte on to the surface of the material. The most popular geometry for wicking or wetting material is fibres, with glass fibre and asbestos traditionally serving these roles. Examples of this technology can be found as early as Billiter who used an asbestos matrix for ionic control in chlorine generating plants in the 1920s. More recently Binder in U.S. Pat. No. 4,036,724 has taught the use of asbestos fibres or aluminum oxide powder to immobilise electrolytes such as perchloric, sulphuric or phosphoric acid. Shaw in U.S. Pat. No. 3,755,125 extended this knowledge to include the use of planar separator discs made from glass fibre with a wick extension that dipped into a liquid electrolyte reservoir. This allowed continuous electrolyte access by the use of separator discs between the electrodes. Separator discs touched at the periphery of their surfaces to allow vertical wicking and four wick extensions into the reservoir allowed excess material to replenish evaporated electrolyte or excess electrolyte in high humidity applications to be stored in the reservoir. Chan et al. (GB 2,094,005) tried to simplify the wicking method, since Shaw used four planar separators, with each displaced 90° relative to the next. Chan et al. employed a hole in the counter electrode with a single annular wick: a simpler design with the added advantage that the wick connecting the reservoir to the working electrode was continuous and did not require pressure between the planar separators to ensure good contact for vertical capillary transport. However, both of these solutions have an excessive number of hydrophilic components to allow adequate electrolyte transport and the single wick in the Chan design is difficult to manufacture and wasteful of electrode material.

Other problems considered in the design of electrochemical gas cells relate not only to the reaction at the working electrode but also to the opposite reaction at the counter electrode and the stabilising reaction at the reference electrode.

The reaction at the reference electrode must be stable with time but does not require generation of a significant current. Therefore the reference electrode can be small and the reaction rates can be slow, so long as the potential resulting from the various reactions is constant. Therefore the reference electrode does not require a large flux of chemicals to create an electrochemically stable environment. The counter electrode, however, must produce a current equal and opposite in sign to the current created by the working electrode. The use of a potentiostatic circuit helps since a potentiostatic circuit is designed specifically to maintain the working electrode at a fixed potential and allow the counter electrode to vary its potential until it finds an electrochemically active species to reduce or oxidise.

When oxidation occurs at the working electrode, the most common reaction at the counter electrode is oxygen reduction but an alternative reaction is hydrogen gas generation. These two reactions are shown below.

$$O_2 + 4H^+ + 4e \Leftrightarrow 2H_2O \quad E^0 = 1.227 \text{ V}$$
$$2H^+ + 2e^- \Leftrightarrow H_2 \quad E^0 = 0.0 \text{ V}$$

An electrochemical gas cell will be limited either by the gas access to and the activity of the working electrode or by the ability of the counter electrode to generate an equivalent balancing current. The first problem is not part of the present invention and has been discussed elsewhere; design of catalytic systems for the working electrodes to respond to specific gases is well known in the art. However the problem of providing adequate oxygen at the counter electrode has received less attention and is commonly solved by three known methods.

Firstly, a counter electrode can be placed below the working electrode with intervening electrolyte whether it is gel, solid or liquid immobilised in a fibrous matrix. Oxygen penetrates through the working electrode, then dissolves into the electrolyte and is transported across the electrolyte to the counter electrode. This method of supplying oxygen to the counter electrode is inherent in the design of nearly every electrochemical gas sensor design but will limit the amount of oxygen accessible to the counter electrode by the thickness of the electrolyte layer, temperature and type of electrolyte and the resultant oxygen solubility in the electrolyte and the rate of diffusion through the electrolyte. Typically in a carbon monoxide sensor a 1 $cm^2$ counter electrode can generate about 300 $\mu A$ of current by oxygen reduction to balance the current generated by the working electrode. At higher current, hydrogen will be reduced.

An alternative method is to allow the two electrodes to be of planar design, with the working electrode having access to the atmosphere under test and the back surface of the counter electrode having access to the same air. Oxygen would then have direct access to the counter electrode in the same way as a working electrode.

The introduction in the 1970s of commercially available gas porous hydrophobic PFTE (polytetrafluoroethylene) polymer materials such as Zytex, and Goretex (Zytex and Goretex are Trade Marks) has given electrochemical cell designers a new opportunity to design flexible gas porous hydrophobic electrodes, providing a barrier to prevent the electrolyte from escaping (due to the hydrophobic properties) but allowing access of oxygen and target gases to a catalyst/binder composition which is laid onto the gas porous support. Coincidentally this also allows radial diffusion of oxygen through the gas porous supports to the under-surface of the catalytic composition of the counter electrode. Solid PTFE or polypropylene supports can also be used, but the diffusion of gas through the solid membranes is much slower and hence access to oxygen is much slower in a solid support than in a gas porous support.

Radial diffusion of oxygen to a counter electrode was taught by Tataria (U.S. Pat. No. 4,184,937). This simple design was the first recorded use of radial gas diffusion using a gas-porous electrode support for the counter electrode. Chan et. al (GB 2,094,005) taught the use of access from the back of the sensor, around an electrolyte reservoir and then through the edges of an electrode stack and radially into the counter electrode. This path is similar to the path as defined by Tataria. However, the use of radial diffusion from the edge to the counter electrode has two problem.

Firstly, if the edge of the electrode stack assembly is enclosed within the sensor housing then channels from the bottom of the sensor housing to the edges of the sensor must be created to allow oxygen access to the edge of the counter electrode. This path can also be an electrolyte leak path, with possible consequent design problems.

Secondly, sealing of an electrode by compression will also compress the electrode support. Increased compression to ensure a more leakproof sensor will lead to reduced oxygen diffusion as gas porosity decreases as the gas porous electrode is compressed.

SUMMARY OF THE INVENTION

According to a first aspect of the present invention there is provided an electrochemical gas sensor including a working electrode for exposure to a gas to be sensed; a counter electrode having an outer periphery; a reservoir for electrolyte; wick means providing a path for electrolyte to pass from the reservoir, around a first part or parts of the outer periphery of the counter electrode to provide electrolytic continuity between the counter electrode and the working electrode; and a gas diffusion means providing a path for gas to diffuse to or from a second part or parts of the outer periphery of the counter electrode.

By having a wick means around part (namely the first part or parts) of the outer periphery of the counter electrode and a gas diffusion means providing a gas diffusion path to or from a different part (namely the second part or parts) of the outer periphery of the counter electrode, a sensor in accordance with the invention enables not only an effective supply of electrolyte to provide electrolytic continuity between the counter electrode and the working electrode but also provides a means for enabling gas to diffuse to or from the counter electrode.

The term "wick means" is used herein to mean means that enables transport of electrolyte. The wick means may be made of material, e.g. fibrous material such as glass fibre, that is porous to liquid or gel electrolyte. Solid state ion exchange materials such as sulphonated PTFE e.g. Nafion (Nafion is a Trade Mark) may also be used.

Preferably, the working electrode, counter electrode and other components are in a layered arrangement, with the working electrode and counter electrode being generally planar in form and stacked upon each other to form an electrode stack assembly. This allows the working electrode and counter electrode to be brought close together in a compact arrangement, whilst having a broad extent to maximise electrochemically active surface area.

Preferably, the counter electrode is sandwiched between two layers of generally planar wick portions that together constitute at least part of the wick means.

A reference electrode may be optionally provided, conveniently located between the counter electrode and working electrode with interposed layers of wick portions.

The layers of wick portions are preferably of larger extent than the counter electrode (and reference electrode if present) and are arranged so as to be in contact with each other around part of the outer periphery (i.e. the first part or parts) of the counter electrode, providing continuity in the path for electrolyte from the reservoir. However, the relative geometries of the wick means and counter electrode are such that the wick means does not fully enclose the counter electrode, leaving exposed part of the outer periphery (i.e. the second part or parts) of the counter electrode which can therefore contact the gas diffusion means. This configuration is achieved by appropriately selecting the shape of the counter electrode and the other components.

The electrode stack assembly may optionally include one or more annular discs of material that is gas porous, hydrophobic and electrically insulating, e.g. polymer materials such as Zytex, Goretex and Mupor (Mupor is a Trade Mark) as referred to above, for electrical insulation purposes, to impart mechanical strength and/or to build up stack thickness. The discs are annular so as not to impede the passage through the stack of electrolyte.

It is generally convenient for the components of the sensor to be circular or disc-like in configuration and coaxially stacked. In this case, the counter electrode should not be circular. Various counter electrode configurations are possible, such as rectangular, semi-circular, cruciform etc., which allow the wick means to pass around a smaller dimension part or parts and the gas diffusion means to contact a larger dimension part or parts.

The working electrode is conveniently supported on a material which is impermeable to electrolyte but permeable to gas. This allows the electrolyte to be retained within the sensor by providing a suitable sealed arrangement whilst enabling the gas to be sensed to penetrate to the working electrode. Microporous PTFE (e.g. Goretex, Zytex or Mupor) is a suitable electrode support material for this purpose. The working electrode can be conveniently formed as a catalytic layer or coating, e.g. of platinum, for instance in the form of a mixture of platinum black and PTFE sintered at elevated temperature, on one surface of the support. The catalytic layer may be formed on only a central portion of the support leaving an annular uncoated edge region of the support, for gas transport and sealing purposes. The catalyst layer is preferably on the side of the working electrode facing the other electrode(s) of the sensor. The counter electrode and reference electrode are conveniently of similar materials and construction, although generally will have a catalytic layer over the full extent of one surface of a support.

Strips or rods of conductive material, e.g. platinum, may be provided in contact with the electrodes in known manner for connection to external circuitry.

The support for the working electrode can also be part of the route by which gas passes to or from the counter electrode. Indeed, the gas diffusion means preferably comprises the support for the working electrode and the support for the counter electrode which are preferably in contact. Gas diffusion is faster where there is contact between the counter electrode support and the working electrode support, so this is preferred, although a small gap that is preferably less than 0.2 mm but may be up to around 1 mm (e.g. 0.5 to 1 mm), across which gas diffuses through the electrolyte may be acceptable in some circumstances where the counter electrode reaction current is small.

Other routes for gas diffusion to and from the counter electrode may also exist, although these will generally not permit such rapid or efficient diffusion and so be of less importance.

It is a possible benefit of this construction that the gas supply to the counter electrode can come from the same gas source to which the working electrode is exposed. Indeed, the sensor preferably has a housing or casing with an aperture through which gas may pass, typically into an air space above the working electrode. In this configuration, it is a benefit that gas from this aperture may diffuse to the counter electrode rather than requiring a separate gas supply around the reservoir, particularly if the sensor is to be mounted on a surface.

Optionally, the reference electrode support is of low gas permeability so as to reduce or eliminate diffusion of interferents to the reference electrode. The reference electrode support may also have means for removing an interferent, such as a metal or metal-organic layer; for example, palladium can be used to remove hydrogen.

The reservoir is conveniently also located within the housing. The reservoir is made from an appropriate electrolyte-resistant material, such as polysulfone or polycarbonate, as it is common to use hostile electrolyte materials such as concentrated acids e.g. sulphuric acid or phosphoric acid. The reservoir desirably includes removable closure means to enable electrolyte to be supplied thereto, for initial use and/or replenishment.

In one preferred embodiment, the sensor is a carbon monoxide sensor, which requires a supply of oxygen to the counter electrode and which uses concentrated sulphuric acid as an electrolyte.

Other possible target gases include sulphur dioxide, hydrogen sulphide and nitric oxide, with the sensor having suitable electrodes for appropriate reaction in each case.

The electrode stack may be assembled and located within the housing together with the electrolyte reservoir, with the components being secured together to form a sealed assembly within which electrolyte can be retained (usually being filled with electrolyte after formation of the sealed assembly, via removable closure means as mentioned above), by virtue of the electrolyte impermeable nature of the working electrode support and by sealing engagement of various components on assembly. The invention can provide a sensor that is easy and cost-effective to manufacture, robust, leak proof and usable in any orientation, while permitting easy access of gas, e.g. oxygen, to or from the counter electrode and reliable transport of electrolyte to the electrodes.

In use the working electrode is exposed (directly or indirectly) to a gas to be monitored, possibly containing a gaseous target analyte such as carbon monoxide to which the sensor is responsive. In the presence of the target gas electrochemical reactions take place in the sensor and the resulting electrical output is monitored in known manner as discussed above. The sensor is preferably in the form of an amperometic electrochemical cell with measurement of current by amperometry. The sensing may be performed qualitatively or quantitatively.

According to a second aspect of the present invention there is provided an electrochemical gas sensor for measurement of a gaseous analyte, the sensor comprising a planar working electrode and a planar counter electrode with electrolyte therebetween, the working electrode and the counter electrode being in contact with the electrolyte, the sensor further comprising a gas diffusion means through which a reagent gas can diffuse to the counter electrode, the gas diffusion means partially or fully enclosing a volume around the working and counter electrodes and having an electrolyte supply means for supply of electrolyte from a reservoir, the counter electrode having an outer edge char-acterised in that part of the outer edge of the counter electrode is in contact with the gas diffusion means and part of the outer edge of the counter electrode is not in contact with the gas diffusion means, there being provided electrolyte transport means for electrolyte to pass around the part of the outer edge of the counter electrode where it is not in contact with the gas diffusion means.

The term "planar" is used in this context to mean an electrode that at least initially was of planar configuration but that may have been deformed somewhat in construction of the sensor.

The counter electrode may contact the gas diffusion means around the outer edge of the top surface and/or outer edge of the bottom surface and/or outer face.

The gas diffusion means may comprise a hydrophobic gas porous support. Preferably, the hydrophobic gas porous support is microporous PTFE.

Preferably, the gas diffusion means may comprise a plurality of separate parts in contact with each other. Part of the gas diffusion means may be a support for the working electrode. Part of the gas diffusion means may be a support for the counter electrode.

The gas diffusion means may further comprise one or more washers such as a stack base.

Preferably, the largest dimension of the counter electrode is less than the inner diameter of the "O" ring seal.

Preferably, the electrolyte is supported by a wicking medium.

Preferably the working electrode and counter electrode are parallel to each other. The working electrode and counter electrode may be coaxial.

The counter electrode may be a rectangle. Alternatively, the counter electrode may be a rectangle with rounded corners or ends. Alternatively, the counter electrode may be a cross.

Alternatively, the counter electrode may comprise a circular central region with one or more arms extending outwards.

The counter electrode catalyst may face the reference electrode.

A reference electrode may be provided in contact with the electrolyte between the working electrode and counter electrode.

The reference electrode and counter electrode may be formed from a single electrode cut into two parts. Preferably, this will form two semi-circles. The semi-circles may not overlap. The reference electrode may be coplanar with the counter electrode. The reference electrode may be formed on the same support as the counter electrode.

The reference electrode may comprise a low or non-gas permeable support, configured to reduce or eliminate diffusion of hydrogen from the counter electrode to the reference electrode. The reference electrode support may have a hydrogen removing means. The hydrogen removing means may be a metal or metal-organic layer. Typically, this will be palladium.

Preferably the gaseous analyte is carbon monoxide and the reagent gas is oxygen. Alternatively the analyte gas may be, e.g., hydrogen sulphide or sulphur dioxide.

The gas diffusion means may be enclosed in a non-porous medium having an aperture therein, the aperture being positioned on the side of the working electrode away from the counter electrode. Preferably, the non-porous medium has no apertures through which gas may penetrate to the gas diffusion means.

Optionally, there may be a small gap between the counter electrode and the gas diffusion means. This may be of the order of 0.5–1 mm, but is preferably less than 0.2 mm.

BRIEF DESCRIPTION OF THE DRAWINGS

The invention will be further described, by way of illustration, with reference to the accompanying drawings, in which.

DETAILED DESCRIPTION OF THE DRAWINGS

FIGS. 1 to 4 illustrates one preferred embodiment of a sensor in accordance with the invention for measuring carbon monoxide in a gas sample.

Figure 1:
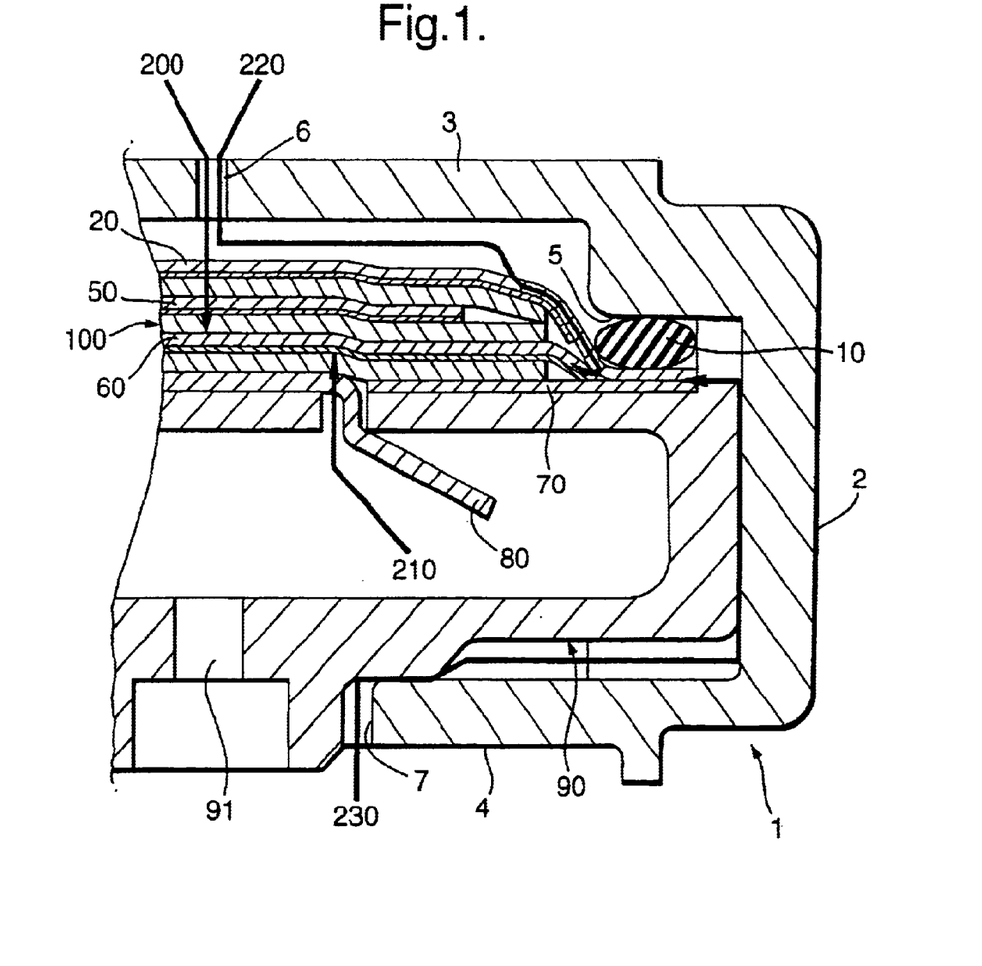
FIG. 1 is a sectional view of part of one embodiment of a carbon monoxide sensor in accordance with the invention.

As shown in FIG. 1, the sensor comprises a generally cylindrical sensor housing or casing 1, made of a corrosion resistant engineering plastics material such as polycarbonate or polysulfone, approximately 25 mm in diameter in which is housed an electrolyte reservoir 90 made of polysulfone or polycarbonate, an electrode stack assembly 100 and a wick 80 of unbound glass fibre, which constitutes hydrophilic non-conductive electrolyte wicking material, extending into the reservoir for contact with electrolyte therein.

Sensor casing 1 has a cylindrical side or two and generally planar circular top and bottom walls, 3 and 4, respectively. The top wall 3 has a stepped configuration and includes an annular shoulder portion 5 around the periphery. A central circular opening 6 passes through the top wall 3 to permit gas passage to the interior of the casing. The bottom wall 4 includes a larger central circular opening 7 through which protrudes part of the reservoir 90, this part including a suitable opening 91 to enable supply of electrolyte to the reservoir.

The casing 1 is conveniently of two-part construction (not shown) for assembly purposes.

Figure 2:
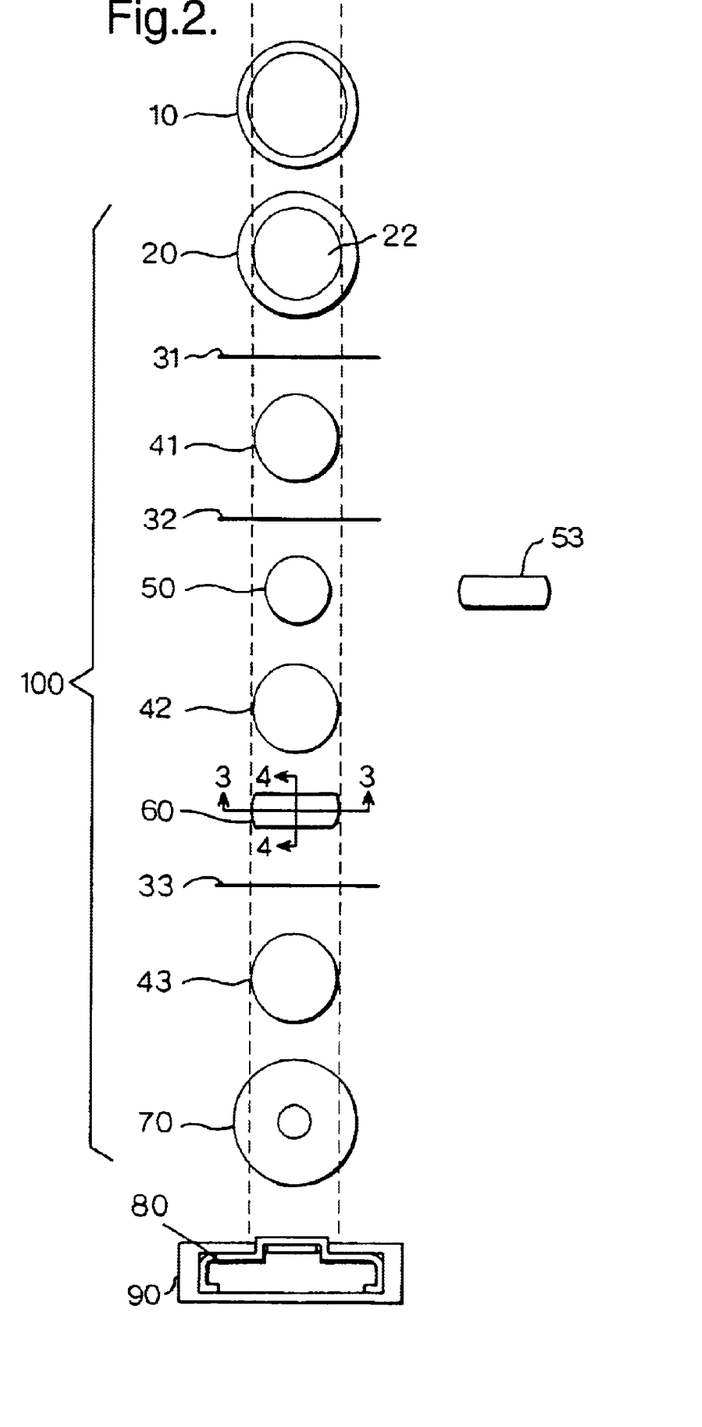
FIG. 2 is an exploded view, on a smaller scale, of the electrode stack assembly of the sensor of FIG. 1.
Figure 3:
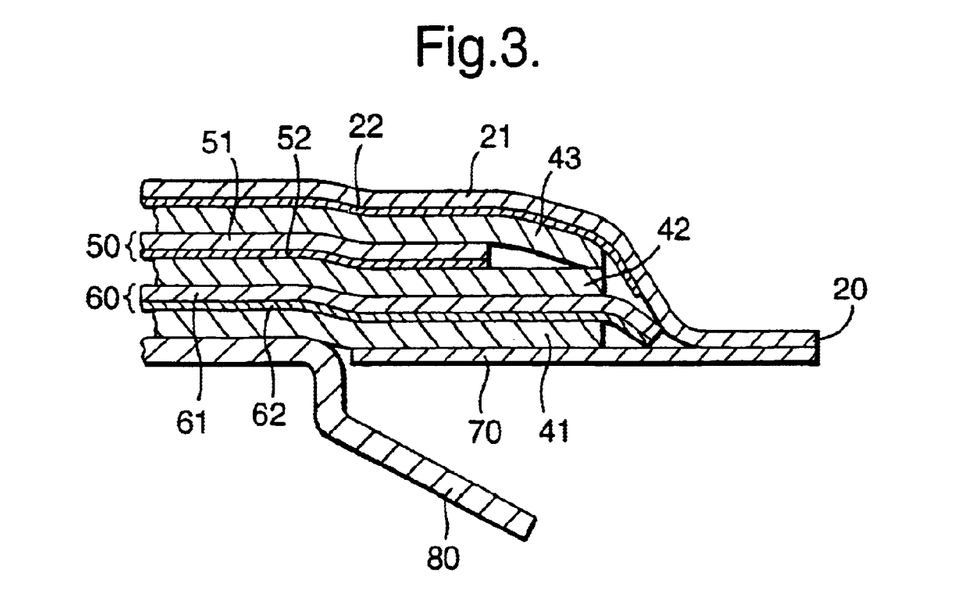
FIG. 3 shows part of FIG. 1, taken along section line 3—3 shown in FIG. 2.
Figure 4:
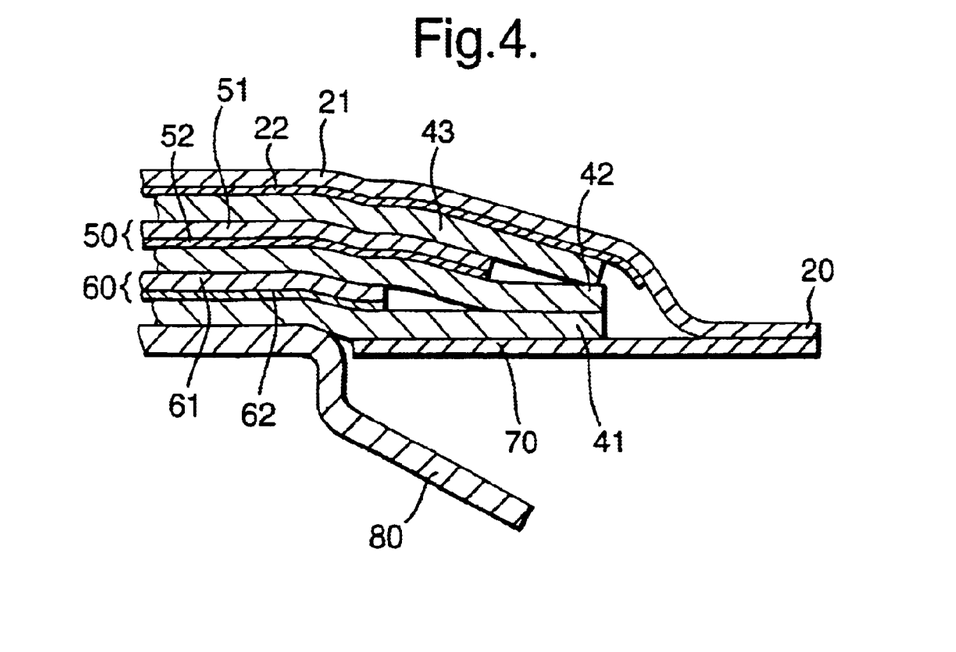
FIG. 4 is a view similar to FIG. 3, taken along section line 4—4 in FIG. 2.

The electrode stack 100 is further illustrated in FIGS. 2 to 4. In FIG. 2, reservoir 90 is illustrated schematically, with the opening 91 omitted for simplicity and wick 80 is shown as lining in a wall of reservoir 90. In FIG. 2, the relative dimensions of the various components are as shown, as illustrated by reference to the dashed guidelines. The components of the electrode stack are generally of planar or sheet-like form, generally being of circular or annular configuration as shown in FIG. 2.

Working from the bottom up as shown in FIG. 2, electrode stack 100 comprises an annular stack base 70 of gas porous hydrophobic PTFE polymer material in the form of Zytex, Goretex or Mupor (Zytex, Goretex and Mupor are Trade Marks). This is followed by a circular separator disc 43 made of unbound glass fibre which constitutes a hydrophilic, non-conductive material permeable to the electrolyte and that functions as electrolyte-wicking material. Then follows a platinum strip or rod 33 that functions as an electrical conductor for connection to a first terminal pin (not shown) on the sensor housing. The assembly then includes a counter electrode 60 that is generally rectangular in plan with rounded shorter edges. Counter electrode 60 comprises a catalytic layer 62 covering the full extent of one face of a hydrophobic microporous PTFE support 61 (e.g. of Zytex, Goretex or Mupor) (see FIGS. 3 & 4). The catalytic layer 62 is formed from a mixture of platinum black catalyst and PTFE binder sintered at elevated temperature to give a porous binder/catalyst material that can be bonded to the support.

The stack then includes a further separator disc 42 similar to separator disc 43. Next in the assembly is circular reference electrode 50 of similar materials and construction by counter electrode 60 and comprising a platinum black/PTFE catalytic layer 52 covering one face of a hydrophobic microporous PTFE support 51. Then follows a second platinum strip 32 similar to strip 33 and leading to a second terminal pin (not shown). A third separator disc 41 similar to discs 43 and 42 is then provided, followed by a third platinum strip 31, similar in construction and function to strips 33 and 32 and leading to a third terminal pin (not shown).

Finally, the electrode assembly includes a circular working electrode 20 again of similar materials and construction to electrodes 60 and 50, comprising a platinum black/PTFE catalytic layer on the circular central portion only of a hydrophobic microporous PTFE support 21 (see FIGS. 3 and 4).

The components of the electrode stack assembly are assembled in order on the reservoir 90 and wick 80 with the electrode catalytic layers on the undersides of the associated supports, facing downwardly towards the reservoir, as shown in FIGS. 1, 3 and 4. An "O" ring 10 is located on top of the assembly, being sized to contact the outer periphery of the working electrode support 21. On insertion of the assembly into the casing 1, as shown in FIG. 1, the casing shoulder 5 contacts the "O" ring 10 which urges the working electrode support 21 into contact with the outer periphery of the stack base 70 and forms a seal, also bringing the various electrode stack components into close contact as shown. During this assembly some of the electrode stack components deform from their initially planar condition, but such components are still to be considered as of planar configuration.

Concentrated sulphuric acid electrolyte is located in the chamber within reservoir 90 for contact with wick 80. The reservoir is not filled completely with electrolyte, leaving a free volume in the reservoir to allow for the possibility of water absorption resulting in an increase in the electrolyte volume, or for water loss through evaporation past the working electrode 20, reducing electrolyte volume. The reservoir may include hydrophilic non-conductive wicking or wetting material to provide a continuous electrolyte path from the reservoir to the separator discs.

Platinum strips 31, 32 and 33 are not shown in FIGS. 1, 3 and 4 for reasons of simplicity and clarity, but are disposed between the relevant layers of the electrode stack assembly to contact the relevant adjacent electrode catalytic layer.

The electrode supports and stack base 70 are all made from hydrophobic microporous PTFE. The hydrophobic properties of the material mean it is impermeable to the electrolyte so that electrolyte is effectively sealed within the housing by virtue of the seal between stack base 70 and the working electrode support 21 produced by "O" ring 10.

The geometry of the various components of the electrode stack is selected so that the separator discs 41, 42 and 43 are of greater extent that the reference electrode and only the smaller dimension (in plan) of the counter electrode. This means that protruding portions of the separator discs are urged into contact as shown in FIGS. 3 and 4. The lower separator disc 43 is also urged into contact with wick 80. The wick 80 and separator discs are all of material that is permeable to the electrolyte, so that these components together constitute wick means providing a path for electrolyte to pass by capillary action from the reservoir to all the electrode catalytic layers, thus providing electrolytic continuity between the electrodes. Passage of electrolyte around the counter electrode is made possible by the counter electrode and associated support in part having a dimension (in plan) that is smaller than that of the adjacent separator discs so that the separator discs can contact each other around these parts of the periphery of the counter electrode, as shown in FIG. 4. This arrangement thus provides for effective passage of electrolyte to all electrodes.

However, the major dimension of the counter electrode and associated support is greater in extent than the adjacent separator discs 42 and 43 so that part of the periphery of the counter electrode protrudes outwardly beyond the separator discs, as shown in FIGS. 1 and 3. The protruding support 61 for the counter electrode contacts the support 21 for the working electrode and stack base 70, as shown in FIG. 3, constituting a gas diffusion means providing a path for oxygen to diffuse to the counter electrode catalytic layer where electrochemical reaction occurs. These components thus constitute the gas diffusion means of the sensor of the present invention.

The reference electrode 50 is fully surrounded by the adjacent separator discs 41 and 42, which reduces the availability of oxygen to the electrode, however this is not usually a problem since the reference electrode generates very little current and hence the dissolved oxygen normally available in the electrolyte is normally adequate to maintain the redox couple at the reference electrode.

An important property of the hydrophobic microporous PTFE support material is that it acts as a barrier to the aqueous electrolyte but is permeable to gases, which can diffuse through the microporous PTFE, enabling oxygen to be supplied to the counter electrode while the materials also seal electrolyte within the sensor.

In use, the sensor is exposed to a gas sample, possibly containing carbon monoxide to be measured and also oxygen, which gains access to the electrodes of the sensor via passage 6. The casing terminal pins are connected to an external potentiostat (not shown), which is used in known manner to set the potential difference of the working electrode with respect to the potential of the reference electrode. The reference electrode provides a standard voltage which, in a potentiostatic circuit, sets the working electrode operating potential. This ensures that the electrochemical reaction at the working electrode is the desired reaction to use the target gas. In the presence of carbon monoxide in the gas sample, carbon monoxide is oxidised at the working electrode, with a corresponding reduction reaction that is believed to be the reduction of oxygen, requiring the supply of oxygen, occurring at the counter electrode. The current resulting from the oxidation of carbon monoxide at the working electrode is measured and used to provide a quantitative reading of carbon monoxide concentration. The catalyst and electrical conditions are selected in known manner so that reaction only occurs in the presence of carbon monoxide and not other gases that may be present in the sample gas.

Oxygen from the surrounding atmosphere can penetrate to the counter electrode by a number of possible routes as illustrated in FIG. 1 by arrows. The main route is indicated by arrow 220 and involves passage of oxygen through working electrode support 21 and counter electrode support 61 which are in contact with each other as shown. This provides a rapid efficient route for oxygen passage, being essentially free of electrolyte, in accordance with the present invention. In a second route shown by arrow 200 oxygen can diffuse through the layers of the electrode stack assembly, dissolving in the electrode. Such diffusion is slow and is known from the prior art (Shaw). In a further route illustrated by arrow 210, oxygen from the residual volume in the reservoir chamber can pass to the counter electrode. Finally, arrow 230 shows yet another route by which oxygen can penetrate through gaps between the casing and reservoir via stack base 70, radially into the electrode under "O" ring 10 to pass into the counter electrode from below. Diffusion may be either Fickian or Knudsen gas diffusion. These various sources of oxygen permit adequate oxygen supply to balance the current generated at the working electrode even at extremely high currents; an example would be 1% carbon monoxide in emissions monitoring.

The illustrated sensor is thus a compact, robust, sealed unit that can be used in any orientation and that has enhanced provision for supply of oxygen to the counter electrode compared with known sensors.

Variants of the embodiment are shown in FIG. 2. In one alternative embodiment the reference electrode may be a strip 53 extending to a diameter less than the "O" ring 10 inner diameter but contacting the working electrode 20 analogously to the design of the counter electrode in order to allow flow of oxygen to the reference electrode. In some circumstances it may be useful for the reference electrode to have direct access to the gases available in the ambient air. For example, if hydrogen is readily available in the air under test then, through the same route as oxygen to the counter electrode, hydrogen could get to the reference electrode changing the preferred chemistry and modifying the electrochemical performance of the sensor: see European Patent Application No. 01304285.8.

Figure 5:
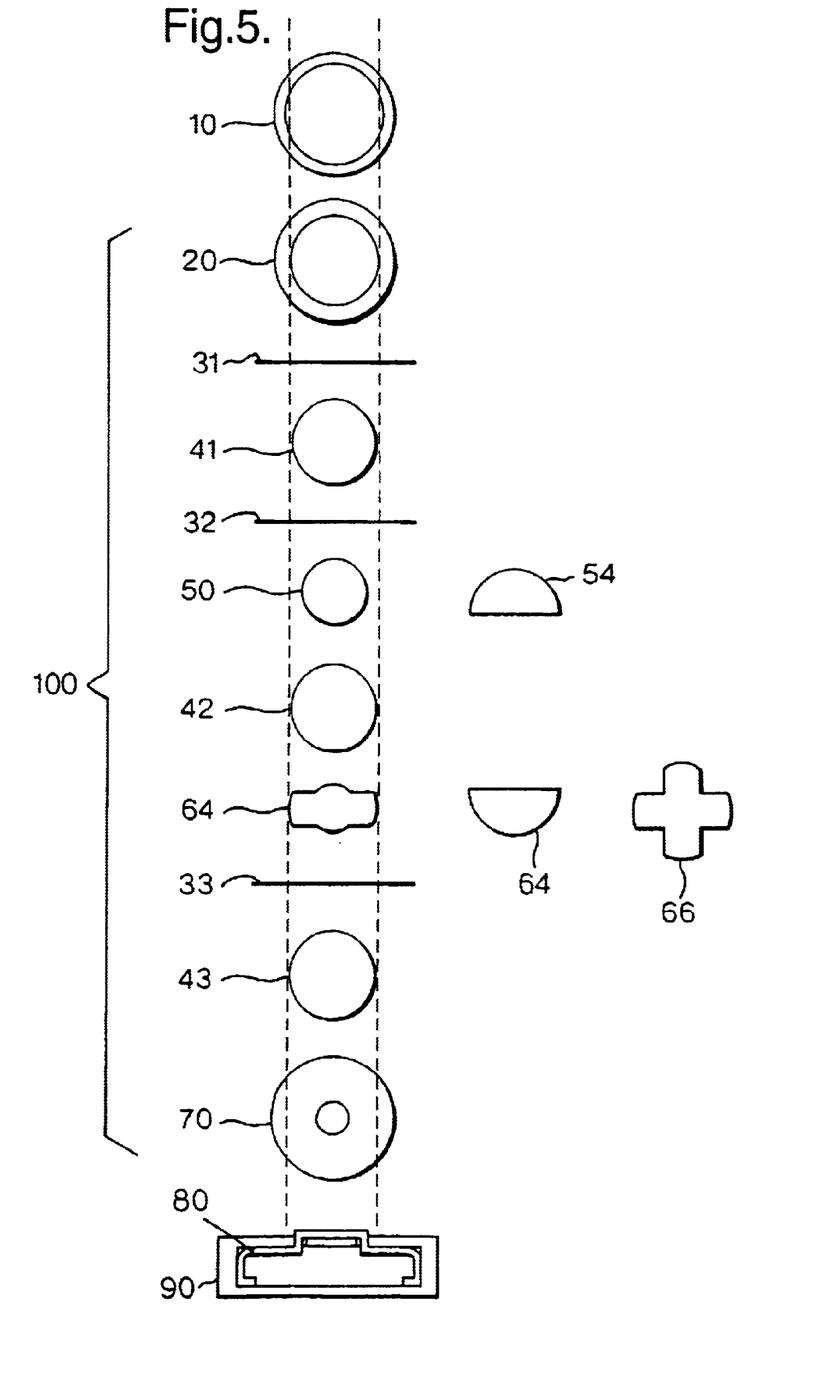
FIG. 5 is a view similar to FIG. 2 illustrating possible alternative electrode configurations.

FIG. 5 illustrates further possible variations. In the main part of the drawing, the illustrated counter electrode 64 is of slightly different configuration, being generally rectangular but including part circular protrusions from the major edges thereof to optimise wicking area while maintaining a high electrode surface area. This variation is of benefit when counter electrode surface area is performance-limiting. In electrochemical sensors where the performance may be improved by increased counter electrode area this geometry will show certain advantages although it may be more expensive to manufacture.

FIG. 5 illustrates another possible variation in which a single disc electrode is manufactured and cut into two components, forming a generally semi-circular counter electrode 65 and generally semi-circular reference electrode 54. The outer periphery of part of both these electrodes may be in contact with the gas permeable support of the working electrode, with the lower electrode also contacting the stack base 70. The disc need not be cut into two similarly sized halves so that the counter electrode 65 and reference electrode 54 do not need to be the same size, and in some cases it may be preferable for them not to be fully semi-circular segments. These variants has the advantage of lower cost of manufacture.

FIG. 5 illustrates a further possible variation of counter electrode configuration, with counter electrode 66 being of generally cruciform configuration. This design maximises oxygen flux to the counter electrode catalyst for applications requiring measurement of very high gas concentrations, such as gas emission measurements.

In a further variant (not illustrated) the reference and counter electrodes can be combined on the same substrate as disclosed in FIG. 3 of U.S. Pat. No. 4,184,937 of Tataria. Advantages include lower cost and simplifying the number of components in the electrode stack assembly, eliminating the reference platinum strip 32, reference electrode 50 and the separator disc 42 between the counter and reference electrodes. The simplicity of design produces a low cost sensor and may be adequate where certain performance criteria are not critical.

The various embodiments of reference electrode and counter electrode may be used in different combinations.

In a further variation the counter electrode may be inverted so that the support is next to the stack base and the catalyst and binder face towards the reference electrode. This eliminates the need for the bottom separator disc. The choice of counter electrode orientation depends on the ability to manufacture reliably and any electrochemical advantages arising from the alternative counter electrode geometry.

There is an additional design parameter which is important when supplying a chemical source to the counter electrode to ensure a stable electrochemical sensor. In a three-electrode system, with potentiostatic control, if the counter electrode does not have adequate oxygen then the counter electrode potential will change, looking for the next species to reduce. In a typical gas sensor design, protons are available from the electrolyte (such as sulphuric or phosphoric acid) to provide the necessary reactants for the counter electrode. So it is predicted and observed that when available oxygen is depleted in typical electrochemical gas cells, the counter electrode will next reduce hydrogen protons, generating hydrogen gas. This will allow the sensor to continue to generate the required counter current, but the by-product of hydrogen gas inside the electrochemical sensor may change the performance of the sensor; this may be a disadvantage to avoid or an enhancement to encourage.

In a further embodiment the reference electrode is disc shaped, and with a solid, low gas permeability polymer support: this solid support reduces the diffusion of any gases generated by the counter electrode, such as hydrogen gas. In this context low gas permeability means sufficiently low permeability that gas diffusion is predominantly Fickian. This shielding of the reference electrode by the support can be enhanced by adding a metal or metal-organic layer which absorbs hydrogen or any other unwanted gas; this layer acts as a buffer to mitigate unwanted surges of hydrogen gas when the sensor is exposed to high gas concentrations.

In a further embodiment an additional gas porous or solid annulus may be added to increase the stiffness of the electrode stack assembly; this would also require additional separator discs.

Further modifications and alterations may be made within the scope of the invention herein disclosed.

What is claimed is:

1. An electrochemical gas sensor comprising:
   a working electrode for exposure to a gas to be sensed;
   a counter electrode having an outer periphery;
   a reservoir for electrolyte;
   wick means providing a path for electrolyte to pass from the reservoir, around a first part or parts of the outer periphery of the counter electrode to provide electrolytic continuity between the counter electrode and the working electrode; and a gas diffusion means providing a path for gas to diffuse to or from a second part of the outer periphery of the counter electrode.

2. A sensor according to claim 1, wherein the working electrode and the counter electrode are in a layered arrangement, with the working electrode and the counter electrode being generally planar in form and stacked upon each other.

3. A sensor according to claim 2, wherein the counter electrode is sandwiched between two layers of generally planar wick portions.

4. A sensor according to claim 1, wherein the working electrode and counter electrode are supported on a material which is impermeable to electrolyte but permeable to gas.

5. A sensor according to claim 4, wherein the electrode support comprises microporous polytetrafluoroethylene.

6. A sensor according to claim 4, wherein the gas diffusion means comprises the support for the working electrode and the support for the counter electrode.

7. An electrochemical gas sensor comprising:

a working electrode for exposure to a gas to be sensed;

a counter electrode having an outer periphery;

a reservoir for electrolyte;

wick means providing a path for electrolyte to pass from the reservoir, around a first part or parts of the outer periphery of the counter electrode to provide electrolytic continuity between the counter electrode and the working electrode; and a gas diffusion means providing a path for gas to diffuse to or from a second part of the outer periphery of the counter electrode, wherein the working electrode and the counter electrode are in a layered arrangement, with the working electrode and the counter electrode being generally planar in form and stacked upon each other, wherein the counter electrode is sandwiched between two layers of generally planar wick portions, and wherein the layers of wick portions are of larger extent than the counter electrode and are in contact with each other around only the first part or parts of the outer periphery of the counter electrode, with the second part or parts of the counter electrode outer periphery extending beyond the wick portions.

8. A sensor according to claim 7, wherein the working electrode and wick portions are generally circular in configuration and coaxially stacked, and the counter electrode is non-circular in configuration.

9. A sensor according to claim 4 further comprising a support for the counter electrode and a support for the working electrode; and wherein the working electrode and the counter electrode are each supported on a material which is impermeable to electrolyte but permeable to gas, with the support for the counter electrode adjacent the second part or parts of the outer periphery, extending beyond the wick portions, and contacting the support for the working electrode, the contacting electrode supports comprising the gas diffusion means.

10. An electrochemical gas sensor comprising:

a working electrode for exposure to a gas to be sensed;

a counter electrode having an outer periphery;

a reservoir for electrolyte;

wick means providing a path for electrolyte to pass from the reservoir, around a first part or parts of the outer periphery of the counter electrode to provide electrolytic continuity between the counter electrode and the working electrode; and a gas diffusion means providing a path for gas to diffuse to or from a second part of the outer periphery of the counter electrode, wherein the working electrode and the counter electrode are in a layered arrangement, with the working electrode and counter electrode being generally planar in form and stacked upon each other, wherein the counter electrode is sandwiched between two layers of generally planar wick portions, and wherein the working electrode and wick portions are generally circular in configuration and coaxially stacked, and the counter electrode is non-circular in configuration.

11. An electrochemical gas sensor comprising:

a working electrode for exposure to a gas to be sensed;

a counter electrode having an outer periphery;

a reservoir for electrolyte;

wick means providing a path for electrolyte to pass from the reservoir, around a first part or parts of the outer periphery of the counter electrode to provide electrolytic continuity between the counter electrode and the working electrode;

a gas diffusion means providing a path for gas to diffuse to or from a second part of the outer periphery of the counter electrode; and a reference electrode.

12. An electrochemical gas sensor comprising:

a working electrode for exposure to a gas to be sensed;

a counter electrode having an outer periphery;

a reservoir for electrolyte;

wick means providing a path for electrolyte to pass from the reservoir, around a first part or parts of the outer periphery of the counter electrode to provide electrolytic continuity between the counter electrode and the working electrode;

a gas diffusion means providing a path for gas to diffuse to or from a second part of the outer periphery of the counter electrode; and a support for the counter electrode and a support for the working electrode, wherein the working electrode and the counter electrode are each supported on a material which is impermeable to electrolyte but permeable to gas and wherein the gas diffusion means comprises the support for working electrode and the support for the counter electrode; and wherein the support for the working electrode and the support for the counter electrode are in contact with each other.

13. An electrochemical gas sensor for measurement of a gaseous analyte, the sensor comprising a planar working electrode and a planar counter electrode with electrolyte therebetween, the working electrode and the counter electrode being in contact with the electrolyte, the sensor having an electrolyte supply means for supply of electrolyte from a reservoir, the sensor further comprising a gas diffusion means through which a reagent gas can diffuse to the counter electrode, the gas diffusion means partially or fully enclosing a volume around the working and counter electrodes, the counter electrode having an outer edge characterized in that part of the outer edge of the counter electrode is in contact with the gas diffusion means and part of the outer edge of the counter electrode is not in contact with the gas diffusion means, there being provided electrolyte transport means for electrolyte to pass around the part of the outer edge of the counter electrode where it is not in contact with the gas diffusion means.

* * * * *

UNITED STATES PATENT AND TRADEMARK OFFICE
CERTIFICATE OF CORRECTION

PATENT NO. : 6,746,587 B2
DATED : June 8, 2004
INVENTOR(S) : John R. Saffell et al.

It is certified that error appears in the above-identified patent and that said Letters Patent is hereby corrected as shown below:

Column 2,
Line 11, change "oxidising" to -- oxidizing --.
Line 18, change "surface active" to -- active surface --.
Line 28, change "mobilises" to -- mobilizes --.
Lines 30 and 35, change "fibres" to -- fibers --.
Lines 30 and 39, change "fibre" to -- fiber --.
Line 35, change "immobilise" to -- immobilize --.
Line 62, change "stabilising" to -- stabilizing --.

Column 3,
Line 10, change "oxidise" to -- oxidize --.
Line 32, change "immobilised" to -- immobilized --.

Column 4,
Line 10, change "problem" to -- problems --.
Lines 58 and 59, change "maxi-mise" to -- maxi-mize --.

Column 6,
Line 67, change "char-acterised" to -- char-acterized --.

Column 7,
Line 1, change "char-acterised" to -- char-acterized --.

Column 8,
Lines 32 and 62, change "fibre" to -- fiber --.

Column 9,
Line 67, change "that" to -- than --.

Column 10,
Line 55, change "oxidised" to -- oxidized --.

UNITED STATES PATENT AND TRADEMARK OFFICE
CERTIFICATE OF CORRECTION

PATENT NO.     : 6,746,587 B2
DATED          : June 8, 2004
INVENTOR(S)    : John R. Saffel et al.

It is certified that error appears in the above-identified patent and that said Letters Patent is hereby corrected as shown below:

Column 11,
Line 45, change "optimise" to -- optimize --.
Line 67, change "maximises" to -- maximizes --.

Signed and Sealed this

Seventh Day of December, 2004

JON W. DUDAS
*Director of the United States Patent and Trademark Office*